United States Patent
Schmidig

(10) Patent No.: US 8,299,792 B2
(45) Date of Patent: Oct. 30, 2012

(54) DEVICE FOR MONITORING A LIVING OBJECT DURING A MAGNETIC RESONANCE EXPERIMENT

(75) Inventor: Daniel Schmidig, Schaffhausen (CH)

(73) Assignee: Bruker Biospin AG, Faellanden (CH)

( * ) Notice: Subject to any disclaimer, the term of this patent is extended or adjusted under 35 U.S.C. 154(b) by 422 days.

(21) Appl. No.: 12/659,237

(22) Filed: Mar. 2, 2010

(65) Prior Publication Data
US 2010/0244826 A1    Sep. 30, 2010

(30) Foreign Application Priority Data

Mar. 30, 2009 (DE) .......................... 10 2009 001 984

(51) Int. Cl.
*G01V 3/00* (2006.01)
(52) U.S. Cl. ...................................... 324/318
(58) Field of Classification Search .......... 324/300–322; 600/410–435
See application file for complete search history.

(56) References Cited

U.S. PATENT DOCUMENTS

| | | | |
|---|---|---|---|
| 4,173,221 A | 11/1979 | McLaughlin | |
| 4,951,672 A | 8/1990 | Buchwald | |
| 5,209,233 A * | 5/1993 | Holland et al. | 600/412 |
| 6,032,063 A | 2/2000 | Hoar | |
| 7,637,907 B2 * | 12/2009 | Blaha | 606/35 |
| 2005/0218897 A1 | 10/2005 | Schulz | |
| 2006/0247509 A1 | 11/2006 | Tuccillo | |
| 2007/0106332 A1 | 5/2007 | Denker | |
| 2008/0132985 A1 | 6/2008 | Wedan | |

FOREIGN PATENT DOCUMENTS

| | | |
|---|---|---|
| EP | 1 923 095 | 5/2008 |
| JP | 04-071536 | 3/1992 |
| WO | WO 02/42790 | 5/2002 |
| WO | WO 02/083016 | 10/2002 |
| WO | WO 03/010551 | 2/2003 |
| WO | WO 2006/031317 | 3/2006 |
| WO | WO 2006/103635 | 10/2006 |
| WO | WO 2006/116677 | 11/2006 |
| WO | WO 2007/047966 | 4/2007 |
| WO | WO 2007/118194 | 10/2007 |
| WO | WO 2008/023321 | 2/2008 |
| WO | WO 2008/051915 | 5/2008 |
| WO | WO 2008/112747 | 9/2008 |
| WO | WO 2008/115426 | 9/2008 |

OTHER PUBLICATIONS

Christina Armenean et al., "RF-Induced Temperature Elevation Along Metallic Wires in Clinical Magnetic Resonance Imaging: Influence of Diameter and Length", Magnetic Resonance in Medicine 52:1200-1206 (2004).

* cited by examiner

*Primary Examiner* — Dixomara Vargas
(74) *Attorney, Agent, or Firm* — Paul Vincent

(57) ABSTRACT

A device for monitoring a living object during a magnetic resonance (MRI) experiment in an MRI tomograph, wherein the device comprises one or more individual electrodes which are connected in an electrically conducting fashion to the living object to be examined, and are connected to a monitoring device via signal lines, wherein each signal line comprises individual parts that are electrically connected to each other via impedances. The eigenfrequencies of these parts are higher than the NMR measuring frequency, preferably more than twice as high, and the parts are electrically connected to each other via frequency-dependent impedances $Z_n$. The electro-magnetic coupling from the RF antenna and the gradient coils to the signal lines can thereby also be minimized in a simple fashion.

11 Claims, 8 Drawing Sheets

DEVICE FOR MONITORING A LIVING OBJECT DURING A MAGNETIC RESONANCE EXPERIMENT

This application claims Paris Convention priority of DE 10 2009 001 984.7 filed Mar. 30, 2009 the complete disclosure of which is hereby incorporated by reference.

BACKGROUND OF THE INVENTION

The present invention concerns a device for monitoring a living object during a magnetic resonance (MRI) experiment in an MRI tomograph, wherein the device comprises one or more individual electrodes which are connected to the living object to be examined in an electrically conducting fashion, and are connected to a monitoring device via signal lines, wherein each signal line comprises individual parts that are electrically connected to each other via impedances.

A device of this type is disclosed in U.S. Pat. No. 4,951,672 A (Reference [7]).

MRI systems are widely used medical and diagnostic devices. The primary components of an MRI system are the magnet that generates a stable and very strong magnetic field (B0), the gradient coils that generate an additional variable magnetic field, and the RF antennas that are used to send energy into the measuring object and to receive the NMR signal from the measuring object. A computer controls the overall process and is required to process the received information.

The object, on which the MRI measurement is carried out, is called patient below. This term explicitly also includes an animal.

In some cases, the patient must be monitored during an MRI examination. This may be required for medical reasons (e.g. for monitoring breathing, the blood oxygen, the body temperature) or also for synchronizing the individual scans of the MRI experiment with physiological changes in the patient (e.g. ECG, EEG or breathing).

MRI experiments, during which the patient is monitored in some way, are called "monitored MRI experiments" below.

For monitored MRI experiments, monitoring electrodes are typically attached to the body of the patient. The electrodes are connected to the monitoring device via signal lines, wherein the monitoring device, in which the signal received by the electrodes is processed and displayed, is often located outside of the electromagnetically shielded MRI region.

The patient is monitored or the MRI experiment is triggered during the MRI measurement. This means that RF pulses or gradient pulses can induce currents in the signal lines. This happens, in particular, when the lines are directly guided through the RF antenna or the gradient, which is often unavoidable.

Coupling Between Gradient and Signal Lines

Currents are induced in conductor loops (e.g. first electrode—body of the patient—second electrode—equivalent impedance of the signal lines) which are permeated by the changing gradient field, wherein the currents can cause heating (e.g. of the contact point between the electrode and the body) and thereby burn the patient.

Coupling Between the RF Antenna and the Signal Lines

The signal lines themselves directly act as antennas which receive the electromagnetic field of the RF antenna. This is called coupling between the signal lines and the RF antenna. Depending on the length and position of the signal lines, this coupling may have a varying strength. During transmission, i.e. during transmission using the RF antenna, i.e. when power is radiated into the system, strong coupling between the RF antenna and the signal lines causes induction of large currents in the signal lines, which, in turn, heats the signal lines, which, in the worst case, can result in burning the patient.

One fact that was neglected in previous publications is that coupling between the RF antenna and the signal lines causes B1 field distortions in the vicinity of the signal lines, causing artefacts in the MRI image or, in the extreme case, also burning the patient. This happens e.g. when the B1 field distortion generates increased local fields in the body of the patient, with the consequence that excessive RF power is deposited at this location, thereby generating an excessive amount of heat. During reception, i.e. when the RF antenna receives signals from the excited nuclear spins, coupling between the RF antenna and the signal lines, in turn, results in inhomogeneous illumination. In the special case, when a phased-array coil is used as an RF antenna, coupling of the individual array coils with the signal lines increases the crosstalk between the individual RF channels and therefore deteriorates the signal-to-noise ratio of the MRI measurement.

Van Genderingen et al (Radiology 1989) describe the use of carbon fibers as ECG lines. The predominant object thereby is to reduce field disturbances of the gradient field, and the associated artefacts when metallic ECG cables are used. The use of carbon fiber ECG lines has become common practice in the meantime. The resistance of carbon fiber lines is in a range of a few hundreds of ohms per meter. This resistance reduces image artefacts due to field interferences of the gradient field, but is not sufficient to prevent heating of the ECG lines due to RF currents or prevent coupling between the RF antenna and the ECG lines to a satisfactory degree.

There are a plurality of publications that follow this idea and try to increase the ohmic resistance of the signal lines by some means.

References [1] to [3] e.g. describe a signal line that is produced through thin film technology and has a resistance of 10,000 ohm/ft. This, however, only deals with the distributed DC resistance of the line.

Reference [4] also describes an ECG line which is especially designed for MRI applications and is intended to prevent heating of the ECG line or the electrode. The ECG line in this case is a spirally wound nickel chromium (Nichrome) wire which has a resistance of 7.5 to 30 kOhm/meter. This patent describes the problem that, when high ohmic resistances are used in the ECG lines, these must be exactly matched to each other to prevent problems with the common mode noise rejection of the ECG device. The described ECG cables are therefore very complex and expensive.

References [5]-[7] describe introduction of one or more discrete ohmic resistances into the signal lines. Reference [7] describes an ECG line that is especially designed for MRI applications, as shown in FIG. 1, which should prevent heating of the ECG line or the electrode. Reference [7] claims that, towards this end, the ECG line must have a high DC resistance and describes how resistances of a magnitude of 33 to 100 kOhm are integrated in the electrode or the ECG cable. The document describes the possibility of dividing the desired resistance into smaller resistances and distributing them over the length of the ECG cable. The central importance of the position and the separations at which the resistances must be disposed is, however, not recognized. Moreover, this patent does not comprehend the coupling mechanism between the ECG line and the RF antenna.

SUMMARY OF THE INVENTION

The inventive device is used to monitor a living object during an MRI experiment in an MRI tomograph, wherein the device comprises one or more individual electrodes which are connected to the living object to be examined in an electrically conducting fashion and are connected to a monitoring device via signal lines, wherein the signal lines comprise individual parts that are electrically connected to each other via impedances.

It is the object of the present invention to minimize electromagnetic coupling from the RF antenna and the gradient coils onto the signal lines.

This object is achieved in a surprisingly simple and also effective fashion in that the eigenfrequencies of these parts are selected to be higher, preferably more than twice as high, as the NMR measuring frequency, and the parts are electrically connected to each other via frequency-dependent impedances $Z_n$.

Minimizing the electromagnetic coupling between the RF antenna and the signal lines yields the following advantages:
  reduced heating of the signal lines and electrodes by the RF power radiated by the RF antenna, thereby preventing burning of the living object to be examined or reducing heating of the living object to be examined
  reduced deterioration of the magnetic field homogeneity of the B1 transmitting or receiving field, therefore generating less additional image artefacts
  fewer excessive RF fields in the body of the living object to be examined, which are generated by the RF antenna and can cause heating or burning of the living object
  less crosstalk between individual phased-array coils, which is caused by the signal lines and can deteriorate the signal-to-noise ratio of the receiving system.

It is not the predominant object of the present invention to eliminate signals which are induced in the signal lines by the MRI experiment (RF pulses; gradient pulses) and cause artefacts in the monitoring signal. This problem can be easily solved by shielding and twisting together the signal lines. However, components are described below, which damp RF currents on the signal lines and at the same time also shield the signal lines from external signals.

The problem of coupling between the signal lines and the RF antenna is not solved by simply mounting a shielding around the signal lines, since in this case, the undesired currents simply flow on the shielding.

Definitions

ω: $\omega = 2\pi f$, wherein f is the nuclear magnetic resonance frequency

L: inductance of a coil

The object of minimizing the coupling between the RF antenna and the signal lines is achieved in that the signal lines between the electrodes and the monitoring device are interrupted to form parts, the parts being connected to each other via impedances. The length of the parts is thereby selected such that the resonance frequency of the parts becomes substantially larger than the NMR resonance frequency, preferably more than twice as large, and that the impedance that connects the parts depends on the frequency.

By selecting the impedance in dependence on the frequency, it is possible to select an impedance that is very high at the NMR resonance frequency (10 to 1000 MHz), but practically acts as short-circuit at the frequency that is interesting for the monitoring signal (<100 kHz).

Coupling between the signal lines and the RF antennas can be minimized through correct selection of the length of the parts and of the frequency-dependent impedance.

Further advantages of the invention can be extracted from the description and the drawing. The features mentioned above and below may be used in accordance with the invention individually or collectively in arbitrary combination. The embodiments shown and described are not to be understood as exhaustive enumeration but have exemplary character for describing the invention.

The invention is shown in the drawing and is explained in more detail with reference to embodiments.

DESCRIPTION OF THE PREFERRED EMBODIMENT

A simple experiment is documented below, which explains and substantiates the above statements.

Towards this end, the resonance circuit of a 300 MHz MRI coil in the unloaded state was optimally adjusted to 50 Ohms. Different free (unearthed) line parts were subsequently introduced into the MRI coil and the mismatch in the resonance circuit of the MRI coil was documented (towards this end, S11 (the reflection coefficient) of the resonance circuit was measured). The MRI coil loaded with the line part was subsequently optimally adjusted and the Q value of the resonance circuit of the MRI coil was determined.

The decrease of the Q value between the unloaded and loaded states is a direct measure of the coupling between the MRI coil and the line in the coil or of the power that dissipates outside of the MRI coil, i.e. into or via the line.

1. Influence of the Length of the Individual Parts

The three following cables are held, one after the other, at exactly the same position in the MRI coil. The parts of the lines are thereby not electrically interconnected.

Figure 1:
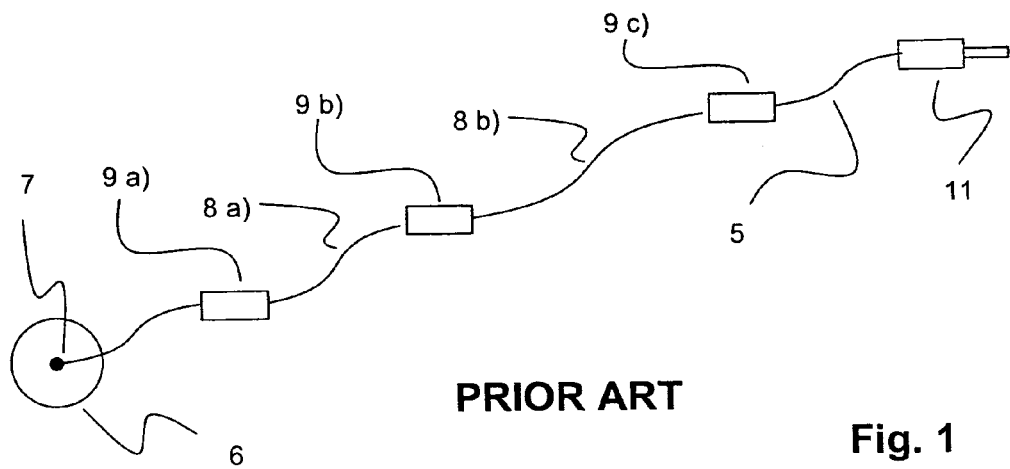
FIG. 1 shows a signal cable for a monitoring signal in accordance with prior art.
Figure 2:
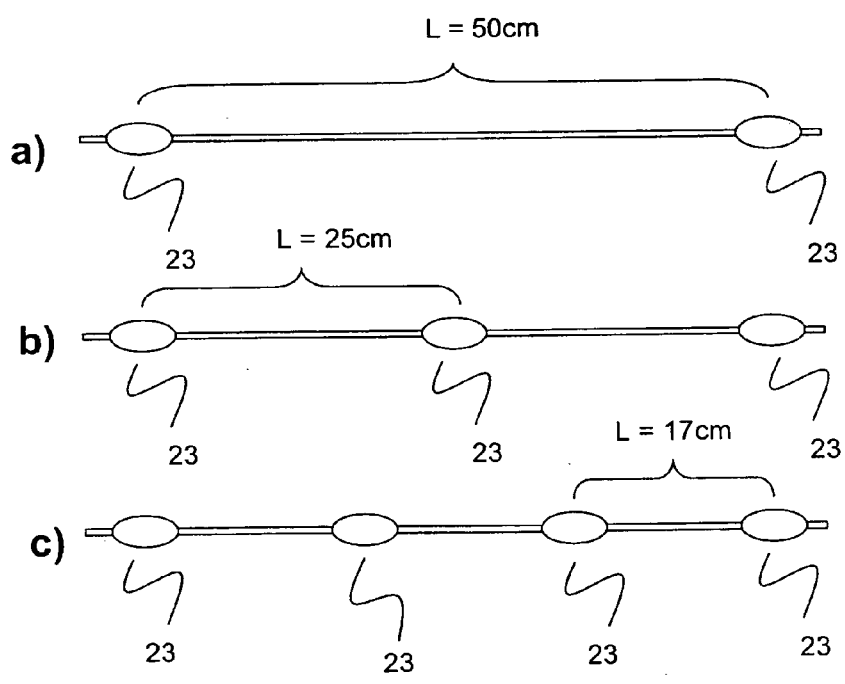
FIG. 2a shows a cable consisting of parts of a length of 50 cm (λ/2 at 300 MHz)
FIG. 2b shows a cable consisting of parts of a length of 25 cm (λ/4 at 300 MHz)
FIG. 2c shows a cable consisting of parts of a length of 16.6 cm (λ/6 at 300 MHz)

1a) cable consisting of parts of a length of 50 cm (λ/2 at 300 MHz), FIG. 2a;
1b) cable consisting of parts of a length of 25 cm (λ/4 at 300 MHz), FIG. 2b,
1c) cable consisting of parts of a length of 16.6 cm (λ/6 at 300 MHz), FIG. 2c.

TABLE 1

Influence of the length of the individual parts

| | Q measured at 300 MHz |
|---|---|
| 1a) | Cannot be measured, since the coil cannot be adjusted |
| 1b) | 69 |
| 1c) | 122 |

The Q value of the unloaded coil was thereby 125 (measured at 300 MHz). The fact that the coupling between the MRI coil and the line decisively depends on the length of the parts is clearly shown. This means that the impedances $|Z_n|$ between the parts can be selected as desired (in the present case: ∞), when the line length of the parts is excessively long, the coupling between the MRI coil and the signal line remains large.

2. Influence of the Impedance $Z_n$ Between the Parts

Figure 3A:
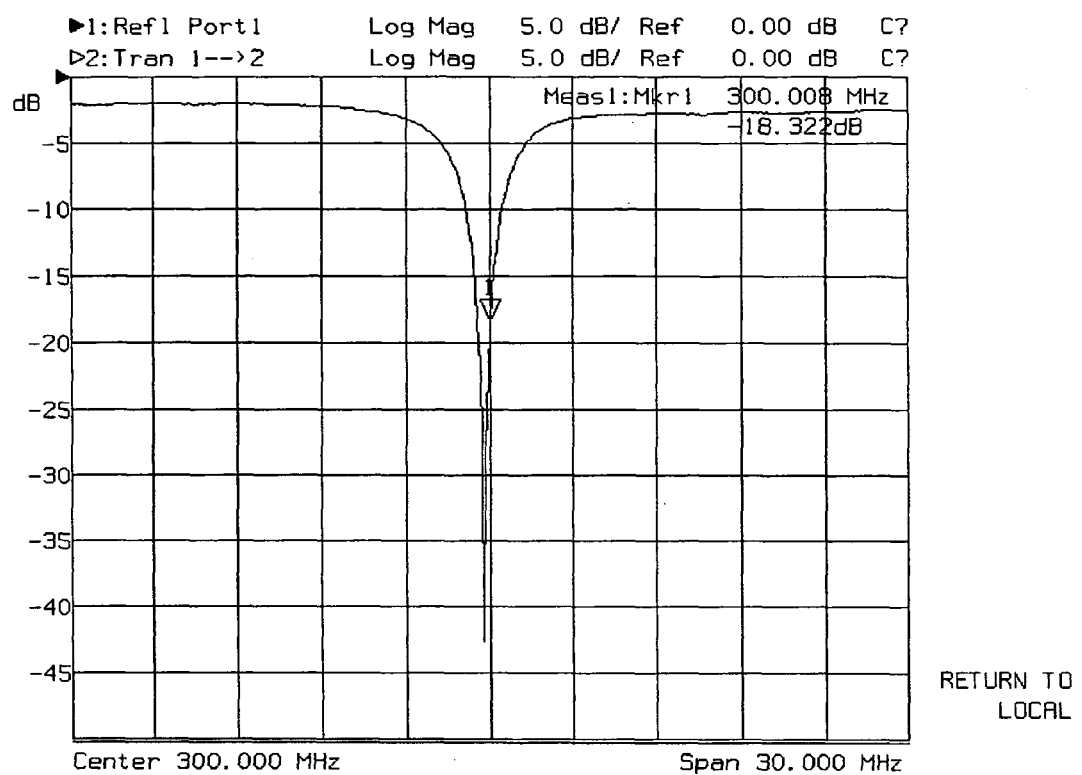
FIG. 3a shows S11 (reflection coefficient) for the resonance circuit of an MRI coil in accordance with experiment 2)a)
Figure 3B:
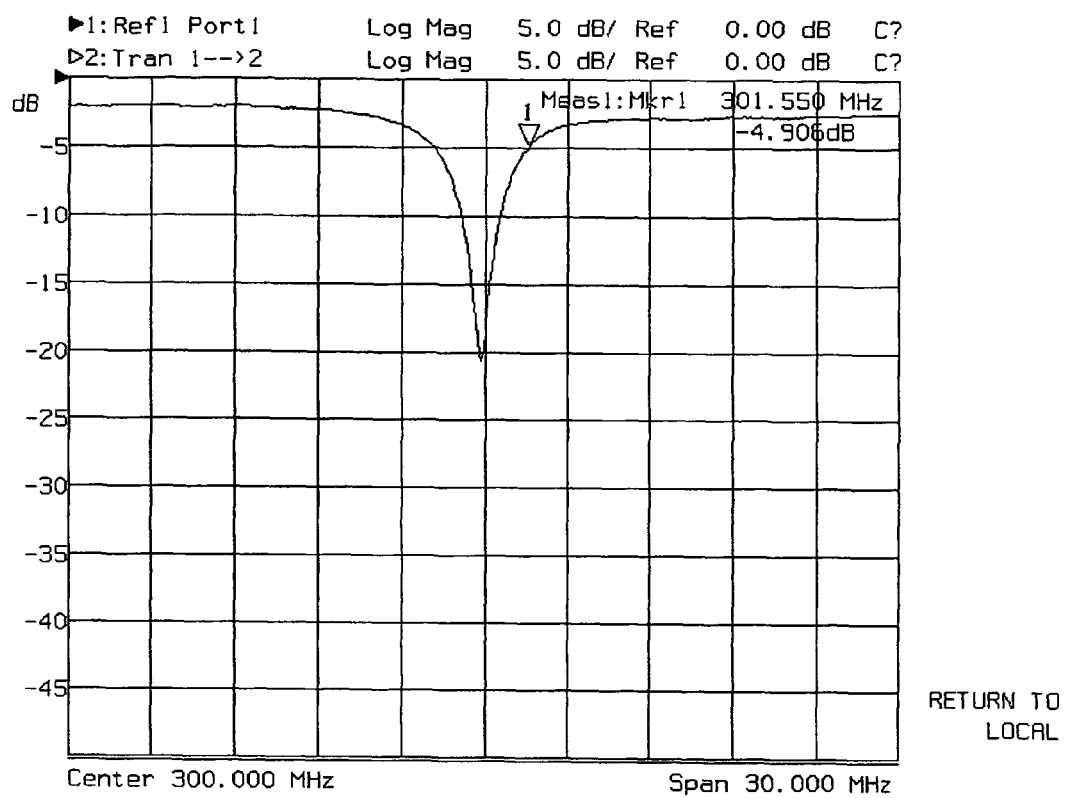
FIG. 3b shows S11 (reflection coefficient) for the resonance circuit of an MRI coil in accordance with experiment 2)c)
Figure 3C:
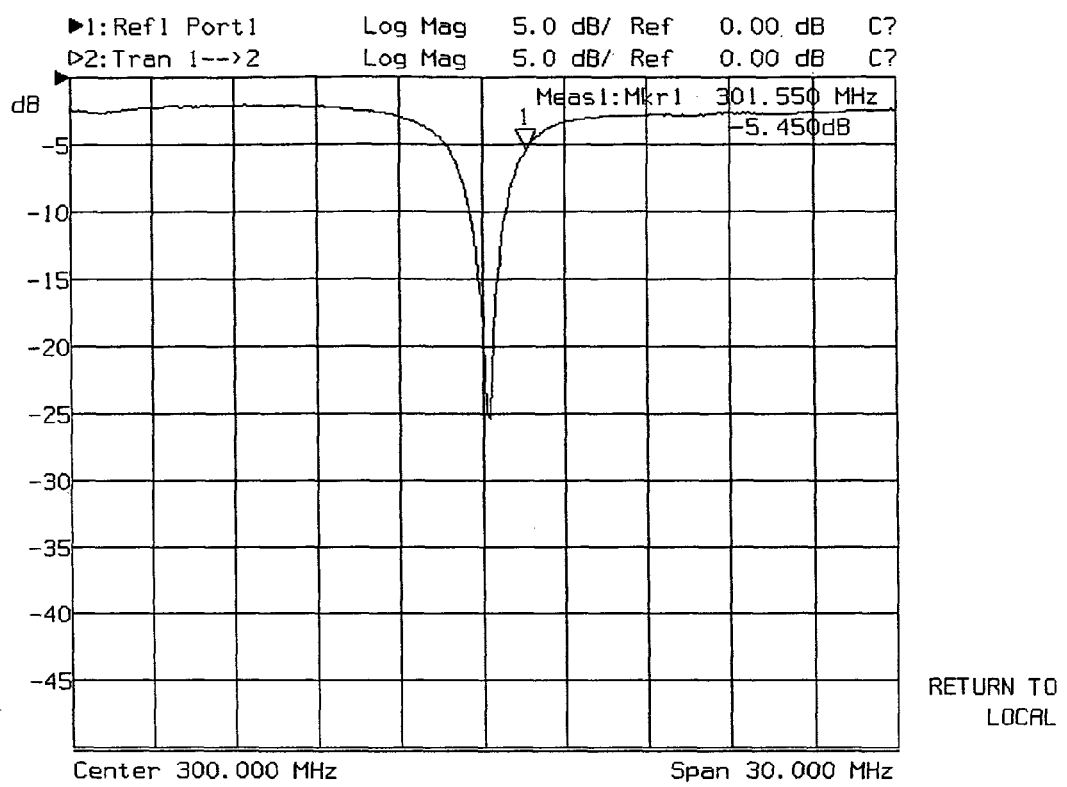
FIG. 3c shows S11 (reflection coefficient) for the resonance circuit of an MRI coil in accordance with experiment 2)d)

A cable consisting of parts of a length of 16.6 cm (λ/6), corresponding to FIG. 2c, is held into the MRI coil. The parts are thereby connected by the following impedances $Z_n$:

2a) electrical interruption (reflection curve shown in FIG. 3a)
2b) ohmic resistance 47 ohms
2c) inductance 1.5 uH (reflection curve shown in FIG. 3b)
2d) rejector circuit (L=28 nH, Q=100) (reflection curve shown in FIG. 3c)

Figure 3D:
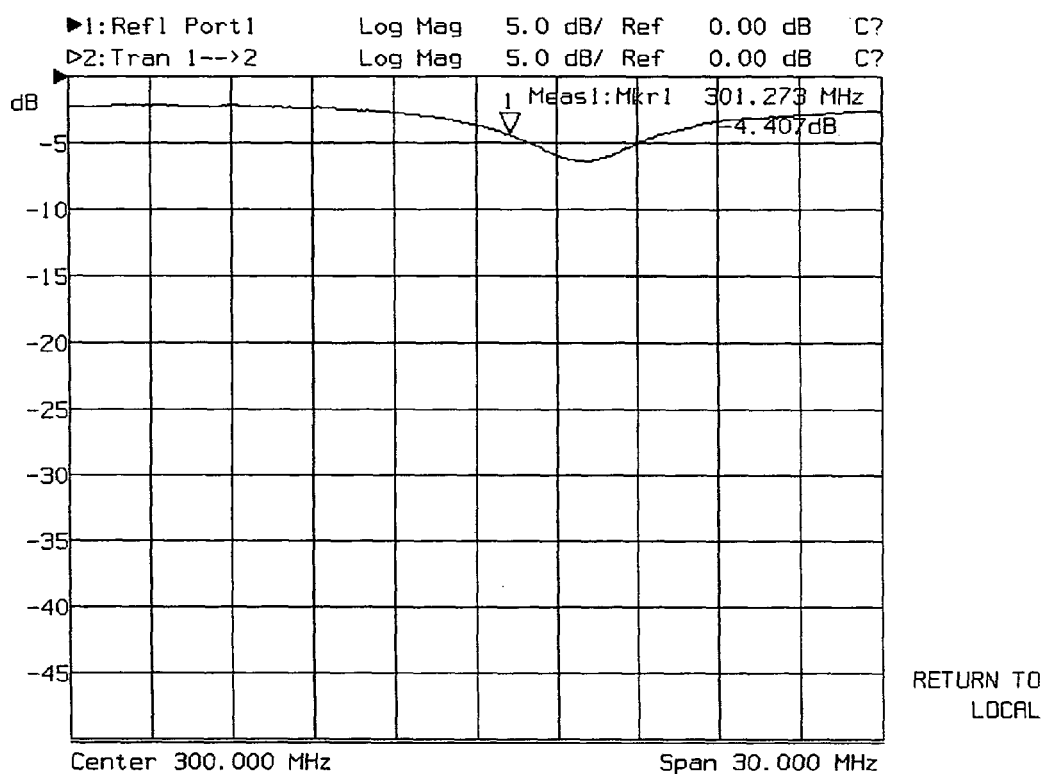
FIG. 3d shows S11 (reflection coefficient) for the resonance circuit of an MRI coil in accordance with experiment 2)e)

The influence of a conventional carbon fiber line (DC resistance: 180 ohms/m) is also stated as a reference:
2e) carbon fiber line (reflection curve shown in FIG. 3d)

TABLE 2 influence of the impedance between the parts

| | $|Z_n|$ at 300 MHz | R | Q measured at 300 MHz |
|---|---|---|---|
| 2a) | ∞ | ∞ | 122 |
| 2b) | 47 ohms | 47 ohms | Cannot be measured since the coil cannot be adjusted |
| 2c) | 2800 ohms | 0.5 ohm | 97 |
| 2d) | 5000 ohms | 0.3 ohm | 114 |
| 2e) | 180 ohms/m | 180 ohms/m | 20 |

The fact that the coupling between the MRI coil and the signal line greatly depends on the impedance $|Z_n|$ of the interruption at the resonance frequency of the MRI coil is clearly shown. The DC resistance R plays a negligible role for the coupling.

Figure 4:
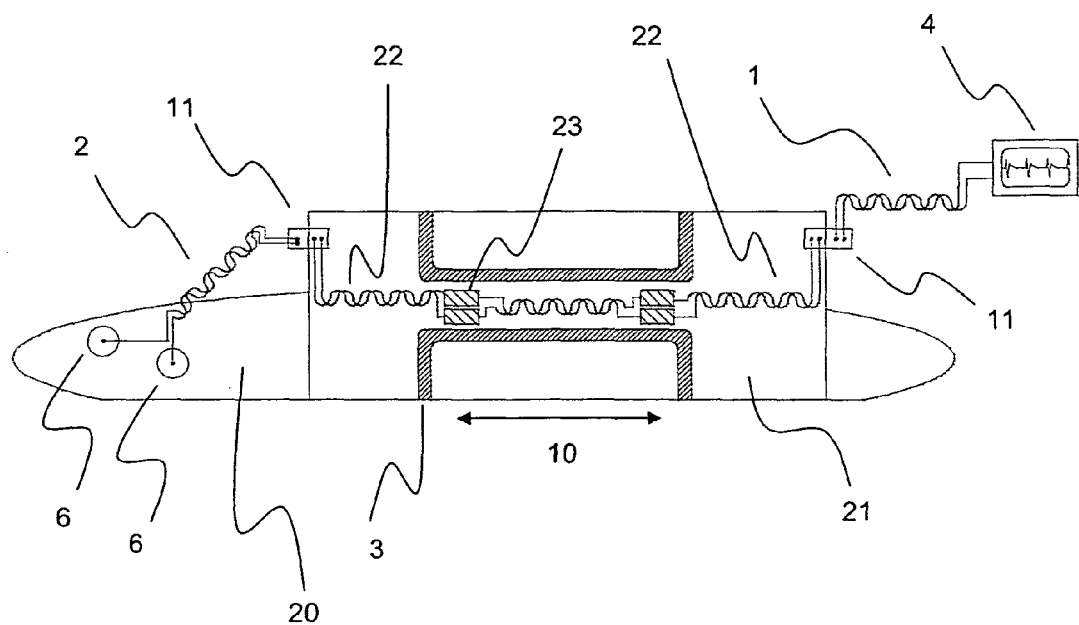
FIG. 4 shows the RF antenna with integrated signal lines.

FIG. 4 shows an inventive device for monitoring a patient during performance of magnetic resonance measurements. The patient is thereby located in the MRI magnet in the RF antenna. At that location where the signal lines are within the field of the RF antenna, they are interrupted at several positions by frequency-dependent impedances and divide the signal line into parts having a length l<λ/2, preferably l<λ/4.

Different embodiments of these frequency-dependent impedances are illustrated in FIGS. 5 through 8.

Devices in accordance with the above description are of interest for suppressing RF currents on the signal line, wherein the reactances of $Z_n$ are substantially larger than their ohmic resistances, in particular, at least twice as large, preferably more than ten times as large as their ohmic resistances. This causes the influence on the high-frequency currents to be large, but the low-frequency monitoring signals, however, are not changed by the impedances $Z_n$.

Devices in accordance with the above description are of special interest for suppressing RF currents on the signal line, wherein the apparent resistances $|Z_n|$ of the frequency-dependent impedances $Z_n$ at the NMR resonance frequency are large ($|Z_n|>500$ ohms) and are small ($|Z_n|<50$ ohms) for frequencies smaller than 100 kHz.

The ohmic resistance of the signal line can therefore be controlled independently of the impedances $Z_n$ by introducing e.g. additional purely ohmic resistances into the line or producing the line itself from suitable materials (e.g. carbon fiber).

Figure 5:
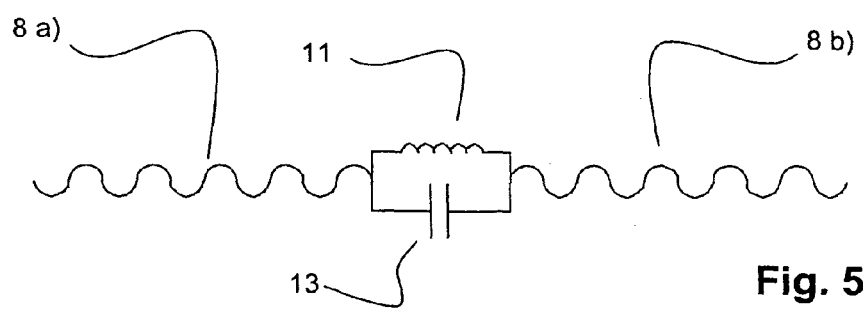
FIG. 5 shows a rejector circuit as frequency-dependent impedance, which divides the signal cable into individual parts.

In one embodiment, shown in FIG. 5, so-called rejector circuits are used for at least part of the impedances $Z_n$, the resonance frequencies of which are adjusted to the NMR measuring frequency.

In the present case, a rejector circuit is shown as an example, which consists of an inductance and a capacitance that is connected in parallel. Assuming that the Q value of the used components is sufficiently large, the RF current has, in the present case, an impedance of an amount $|Z_n| \approx Q\omega L$. The ohmic resistance simply corresponds to the ohmic resistance of the inductance. Since these rejector circuits themselves are resonant at the NMR resonance frequency, there is the danger that the rejector circuits themselves couple with the MRI coil. In order to prevent this, the rejector circuits must either be shielded or orientated in such a fashion that their field is orthogonal to the field of the MRI coil.

Figure 6:
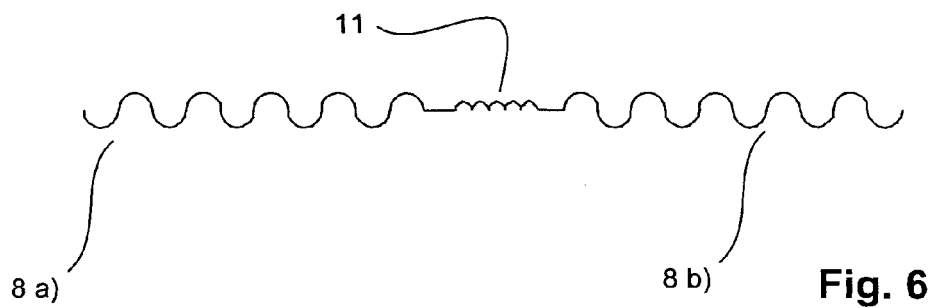
FIG. 6 shows the inductance as frequency-dependent impedance, which divides the signal cable into individual parts.

In a more straightforward embodiment shown in FIG. 6, simple inductances are used for at least part of the impedances $Z_n$. This inductance acts as an impedance of the amount $|Z|=\omega L$ for the RF current. The ohmic resistance simply corresponds to the ohmic resistance of the wire from which the inductance is wound.

Figure 7:
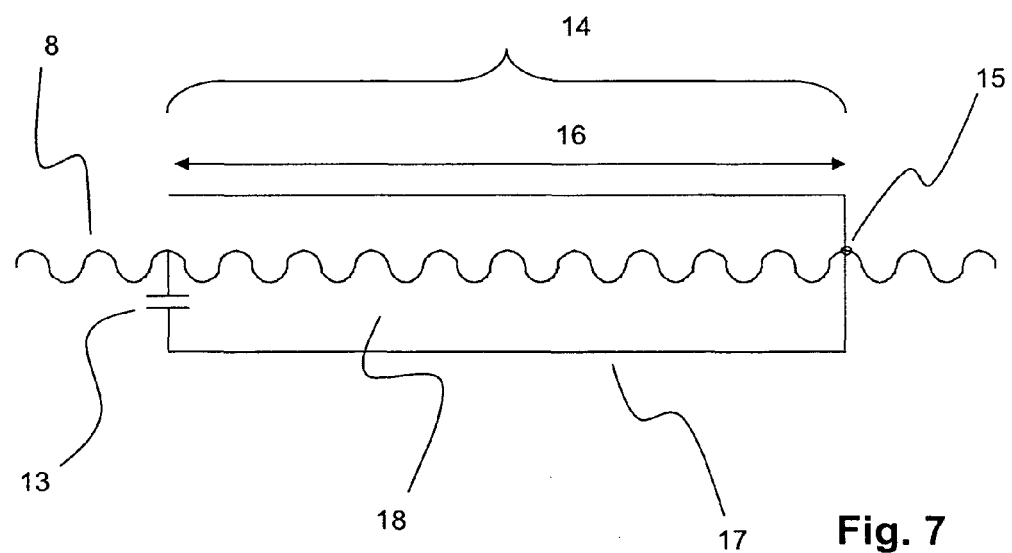
FIG. 7 shows a shortened Bazooka Balun as frequency-dependent impedance, which divides the signal cable into individual parts.
Figure 8:
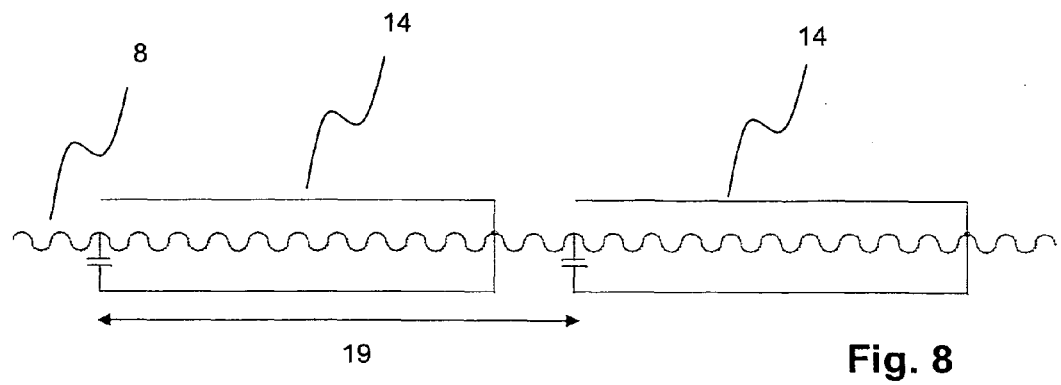
FIG. 8 shows a Bazooka Balun Array as frequency-dependent impedances, which divides the signal cable into individual parts.

In one further embodiment, shown in FIG. 7, "Bazooka Baluns" are used for at least part of the impedances $Z_n$, which are disposed one behind another and contain the signal lines. The advantage thereof consists in that the signal line extends over long distances inside the outer jacket and is thereby additionally shielded against coupling-in of signals into the signal line. The signal line can then practically be completely shielded by disposing several Bazooka Baluns one after the other (see FIG. 8).

All described RF components damp RF currents on the signal lines and thereby prevent coupling between the RF antenna and the signal lines.

It may then be advantageous to mechanically mount the signal lines in the area of the RF antenna of the MRI receiving system on the carrier of the RF antenna within the inventive device. This causes the residual influence of the signal lines on the RF antenna to remain constant and can be compensated for within the RF antenna. The position of the signal lines on the carrier of the RF antenna can additionally be experimentally selected such that the electromagnetic coupling between the RF antenna and the signal lines is minimized.

FIG. 4 shows that, when signal lines are mounted to the carrier of the RF antenna, it is possible to use plugs for electrically connecting the signal lines from the patient or monitoring device to the signal lines that are mounted to the carrier of the RF antenna. In consequence thereof, the preparation of the patient is often substantially simplified, since the signal lines no longer have to be guided through the RF antenna.

Figure 9:
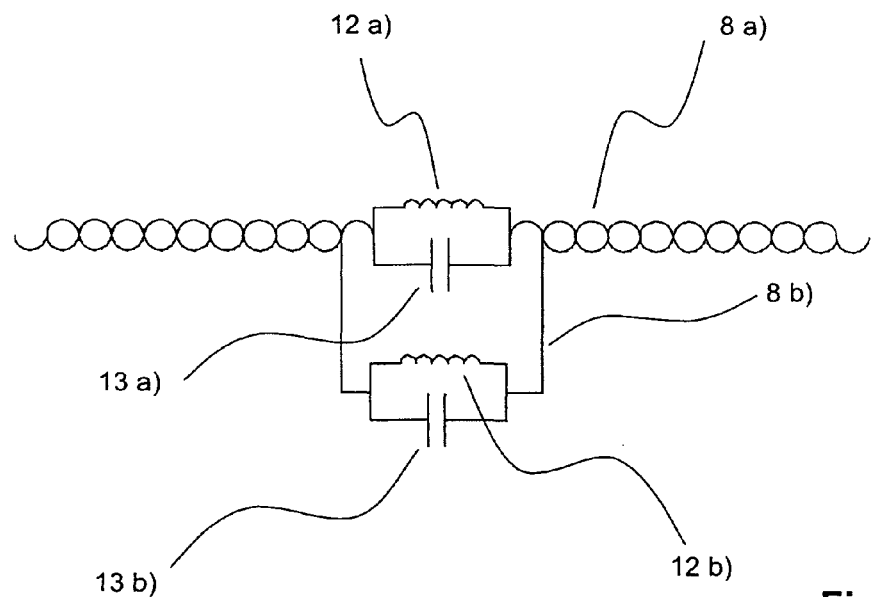
FIG. 9 shows several ECG cables and the arrangement of the individual parts with respect to each other.

Normally, more than one signal line is connected to the patient. In this case, attention must be paid that signal lines with the same distribution of parts are used, wherein these signal lines are positioned in such a fashion that the corresponding parts are disposed next to each other. Alternatively, there is the possibility that the impedance of a cable is short-circuited by the cable of another line for RF currents and therefore becomes ineffective. The neighboring parts of the signal lines should be twisted together in order to minimize signal coupling into the signal lines. FIG. 9 shows the described arrangement of impedances and parts of the signal line for the special case of two signal lines.

List of Reference Numerals

| | |
|---|---|
| 1 | signal cable between the RF antenna and the monitoring device |
| 2 | signal cable between the patient and the RF antenna |
| 3 | RF antenna |
| 4 | monitoring device |
| 5 | signal cable between the monitoring electrode and the monitoring device |
| 6 | monitoring electrode |
| 7 | contact point monitoring electrode-signal cable |
| 8 | part of the signal cable between monitoring electrode monitoring device |
| 9 | ohmic resistance which separates the individual parts from each other |
| 10 | distance between two impedances |
| 11 | signal cable plug |
| 12 | inductance |
| 13 | capacitance |
| 14 | Bazooka Balun |
| 15 | conducting contact point between signal cable and outer conductor Bazooka Balun |
| 16 | length of the Bazooka Balun |
| 17 | outer conductor of the Bazooka Balun |
| 18 | dielectric between the outer conductor and the inner conductor of the Bazooka Balun |
| 19 | separation between two Bazooka Baluns |
| 20 | patient |
| 21 | carrier RF antenna |
| 22 | signal cable mounted to the carrier of the RF antenna |
| 23 | impedance that separates the parts of the signal line from each other |

List of References

[1] US 2006/0247509 A1 (ECG Cable for use in MRI)
[2] WO 2006/116677 A2
[3] WO 2006/116677 A3 ("search report" relating to US 2006/0247509 A1 (ECG cable for use in MRI))
[4] U.S. Pat. No. 6,032,063 A (Distributed resistance leadwire harness assembly for physiological monitoring during magnetic resonance imaging)
[5] JP 4071536 A
[6] U.S. Pat. No. 4,173,221 A (ECG Cable monitoring system)
[7] U.S. Pat. No. 4,951,672 A (Controlled impedance monitoring lead wires)

I claim:

1. A device for monitoring a living object during a magnetic resonance (MRI) experiment in an MRI tomograph, the device comprising:
   one or more individual electrodes which are connected in an electrically conducting fashion to the living object to be examined;
   a monitoring device; and
   signal lines disposed between and connecting said electrodes to said monitoring device, each signal line comprising individual parts that are electrically connected to each other via impedances, wherein eigenfrequencies of said parts are higher than an NMR measuring frequency, said parts being electrically connected to each other via frequency-dependent impedances ($Z_n$).

2. The device of claim 1, wherein said eigenfrequencies of said parts are more than twice as high as said NMR measuring frequency.

3. The device of claim 1, wherein reactances of said frequency-dependent impedances $Z_n$ are larger than ohmic resistances thereof.

4. The device of claim 3, wherein said reactances at least twice as large or more than ten times as large as said ohmic resistances thereof.

5. The device of claim 1, wherein, for said impedance $|Z_n|$ of said frequency-dependent impedances $Z_n$, $|Z_n|>500$ ohms for the NMR resonance frequency and $|Z_n|<50$ ohms for frequencies smaller than 100 kHz.

6. The device of claim 1, wherein rejector circuits are used for at least one part of said impedances $Z_n$, said rejector circuits having resonance frequencies which are adjusted to said NMR measuring frequency.

7. The device of claim 1, wherein at least one part of said impedances $Z_n$ have inductances.

8. The device of claim 1, wherein at least one part of said impedances $Z_n$ comprises Bazooka Baluns which are disposed one behind an other and contain said signal lines to said electrodes in interiors thereof.

9. The device of claim 1, wherein said signal lines are mechanically mounted to a carrier of an RF antenna in an area of said RF antenna of an MRI receiving system.

10. The device of claim 9, wherein positions of said signal lines on said carrier of said RF antenna are selected by means of experiments such that an electromagnetic coupling between said RF antenna and said signal lines is minimized.

11. The device of claim 1, wherein several signal lines with a same distribution of parts are provided, said signal lines being positioned in such a fashion that corresponding parts are disposed next to each other.

* * * * *